United States Patent [19]

Buendia et al.

[11] Patent Number: 4,812,512
[45] Date of Patent: Mar. 14, 1989

[54] SUPPORTS AND THEIR USE

[75] Inventors: Jean Buendia, Le Perreux Sur Marne; Jeanine Nierat, Suresnes, both of France

[73] Assignee: Roussel Uclaf, France

[21] Appl. No.: 878,611

[22] Filed: Jun. 26, 1986

[30] Foreign Application Priority Data

Jun. 27, 1985 [FR] France ................ 85 09786

[51] Int. Cl.$^4$ .................. C12P 18/34; C12P 18/38
[52] U.S. Cl. .................. 525/54.11; 525/54.2; 525/326.6; 525/327.7; 525/327.5; 530/334; 536/24; 536/25; 536/26; 536/27; 536/28; 536/29; 536/121; 252/62.54; 252/62.56; 556/419; 556/420; 556/421; 556/422; 564/79; 564/80; 564/82; 564/89
[58] Field of Search ............. 525/54.11, 54.2, 326.6, 525/327.7, 327.2, 327.5; 530/333, 334; 536/22, 23, 24, 25, 26, 27, 28, 29, 18.5, 121; 514/7, 76; 252/62.51, 62.54, 62.56; 556/419, 420, 421, 422; 564/79, 80, 82, 89, 98, 99

[56] References Cited

U.S. PATENT DOCUMENTS

| 4,591,614 | 5/1986 | Miller et al. | 514/76 |
| 4,638,032 | 1/1987 | Benner | 525/54.1 |
| 4,659,774 | 4/1987 | Webb et al. | 525/333.4 |

Primary Examiner—Morton Foelak
Assistant Examiner—Nathan M. Nutter

Attorney, Agent, or Firm—Bierman & Muserlian

[57] ABSTRACT

Novel supports useful in solid phase synthesis of oligonucleotides of the formula

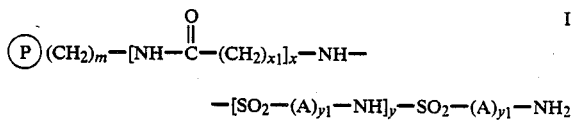

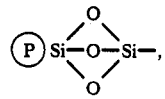

wherein Ⓟ is a material selected from the group consisting of functionalized glass micropellets, silica functionalized by aminoalkyl trialkoxysilane capable of to obtain for Kieselguhr, polytetrafluoroethylene, cellulose and metallic oxides, m is an integer from 1 to 20, A is selected from the group consisting of alkyl of 1 to 20 carbon atoms, saturated cycloalkyl of 3 to 12 carbon atoms, phenyl and 5 to 6 member heterocycles, x and y are an integer from 0 to 20, $x_1$ is an integer from 1 to 20 and $y_1$ is an integer from 0 to 10, a process for the preparation of said supports, the use of said supports and intermediates.

11 Claims, No Drawings

SUPPORTS AND THEIR USE

STATE OF THE ART

Many supports useful in the synthesis of oligonucleotides in the solid phase have been described in the literature. Examples of these supports are polymers such as polystyrene described in Nucleic. Ac. Res., Vol. 8, 1980, polyacrylamide acryloylmorpholide and polydimethylacrylamide polymerized onto Kieselguhr described in Nucleic Ac. Res., Vol. 9(7), 1981, p. 1691 of the formula Kieselguhr polyacrylamide

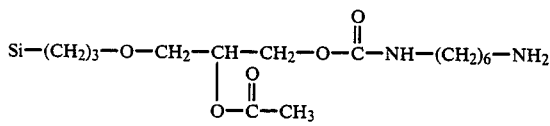

However, these supports have the disadvantage that they have a tendency to excessively swell and retain certain reactants.

Supports of an inorganic nature have also been described in the literature such as supports of the formula

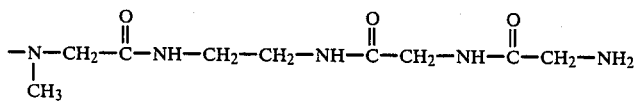

described in J.A.C.S., Vol. 105 (1983), p. 661 and silica based supports made functional by a 3-aminopropyl triethoxysilane group described in European Pat. No. 0,035,719 as being useful in the phosphite and phosphoramidite synthesis for the preparation of oligonucleotides. However, the latter support gives poor yields when used in the phosphotriester synthesis, particularly in the first couplings.

OBJECTS OF THE INVENTION

It is an object of the invention to provide novel improved supports for preparation of olignonucleotides and a process for the preparation of said supports.

It is another object of the invention to provide a novel process for the preparation of oligonucleotides and novel intermediates formed therein.

These and other objects and advantages of the invention will become obvious from the following detailed description.

THE INVENTION

The novel supports of the invention have the formula

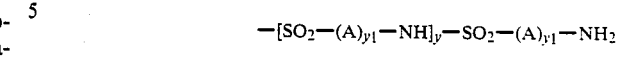

wherein Ⓟ is a material selected from the group consisting of functionalized glass micropellets, silica functionalized by aminoalkyl trialkoxysilane capable of to obtain for

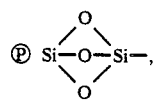

Kieselguhr, polytetrafluoroethylene, cellulose and metallic oxides, m is an integer from 1 to 20, A is selected from the group consisting of alkyl of 1 to 20 carbon atoms, saturated cycloalkyl of 3 to 12 carbon atoms, phenyl and 5 to 6 member heterocycles, x and y are an integer from 0 to 20, $x_1$ is an integer from 1 to 20 and $y_1$ is an integer from 0 to 10.

Examples of A as alkyl of 1 to 20 carbon atoms are methyl, ethyl, propyl, butyl, hexyl, octyl, decyl, dodecyl and alkyl substituted with one or more methyl or ethyl groups such as methyl-1-methane-diyl; methyl-1-ethane-diyl-1,2; methyl-1 or 2-propane-diyl-1,3; methyl-1,2-propane-diyl-1,3 and ethyl-1-diyl-1,2.

Examples of A as a saturated cycloalkyl are cyclopropane, cyclobutane, cyclopentane, cyclohexane, cycloheptane, cyclooctane, cyclononane, cyclodecane, cycloundecane and cyclododecane and examples of A as a heterocycle of 5 to 6 members are thiazolyl, pyridinyl, 4,5-dihydrothiazolyl, oxazolyl, isoxazolyl, imidazolyl, pyrmidyl or thienyl.

By "functionalized" in the case of the glass micro-pellets, it is understood that the groups in question have a terminal amino function which enables an easy fixation of groups containing sulfonamide functions.

Examples of preferred supports of formula I are those of the formula

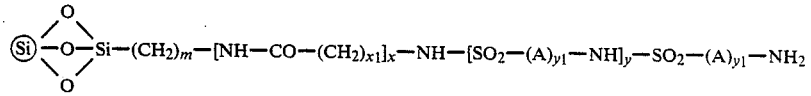

and those of the formula

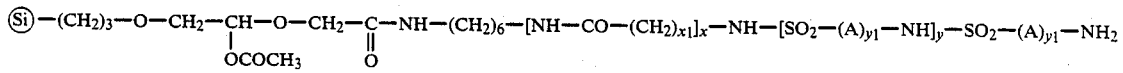

wherein m, $x_1$, x, $y_1$, A, y are defined as above.

Particularly preferred supports of formula I are those wherein Ⓟ is a support having a homogeneous particle size. Commercial silica can be used, for example VYDAC silica A having grains of which the diameter is 20μ and pores 300 Å. Any other silica comparable to silica VYDAC A Ⓡ can be used. There can also be used a silica for chromatography, a silica HPLC, for example the silica marketed under the name of porosil B ®, the grain diameter of which is between 37 and 75μ.

Preferred supports of formula I are those wherein ⓟ is a support having a homogeneous particle size, and for which m is a whole number from 1 to 10 and $x_1$ is a whole number from 1 to 10 and x is a whole number from 0 to 10 and more particularly, the supports of formula I wherein A is a —CH$_2$— or phenyl, those wherein $y_1$ is a whole number from 0 to 5 and y is a whole number from 0 to 10, and those for which, where ⓟ is a group

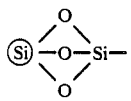

and m=3.

Specific supports of the invention are those having the formulae

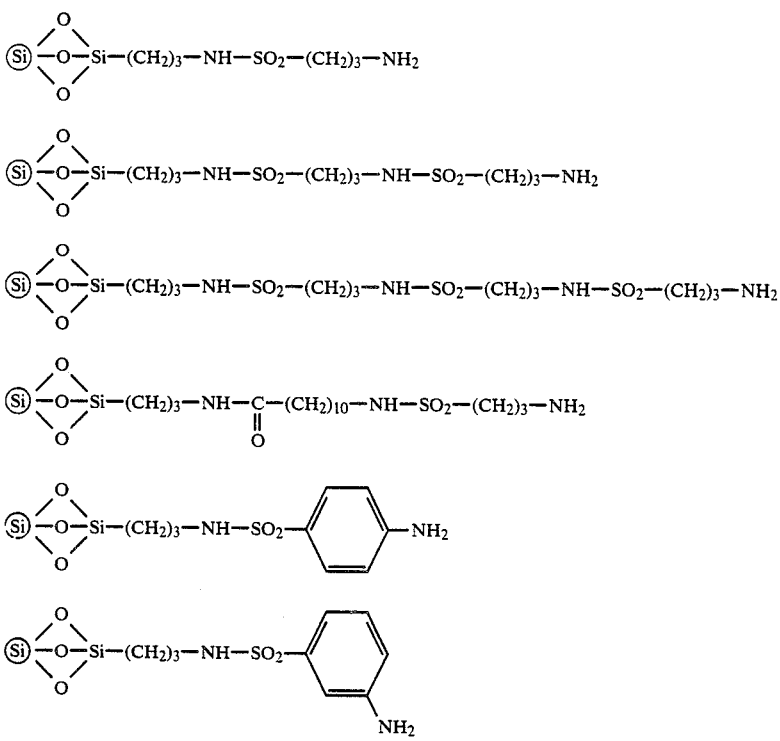

Si being a silica VYDAC A or an equivalent silica as well as the support of the formula

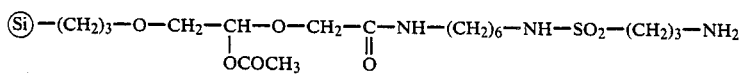

(derivative of the glass C.P.G./LCAA or Controlled Pore Glass Long Chain Alkyl Amine ®).

The invention also concerns a process for the preparation of supports of formula I comprising reacting a compound of the formula $$RN-(A)_{y1}-SO_2Cl \quad \text{II}$$

wherein R is a monovalent or divalent protective group of the amine function, A and $y_1$ having the above definition in the presence of a tertiary amino base with either a support of the formula

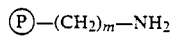

wherein ⓟ and m have the above definition to obtain an intermediate support of the formula

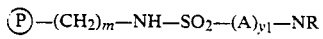

of which the end —NH$_2$ group is liberated to obtain thus a support of formula I in which ⓟ, m, A, $y_1$ have the previous significances, and in which x=0 and y=0, which support, if necessary, is reacted again with a product of formula II under the same conditions as before to obtain an intermediate support of the formula ⓟ—(CH$_2$)$_m$—NH—SO$_2$—(A)$_{y1}$—N-
H—SO$_2$—(A)$_{y1}$—NR which the end group —NH$_2$ is liberated again to obtain a support of formula I in which x=0 and y=1, which process, if necessary, is continued successively, passing through the intermediate supports with the formula ⓟ—(CH$_2$)$_m$—NH—[SO$_2$—(A)$_{y1}$]$_y$—SO$_2$-
(A)$_{y1}$—NR in which R, ⓟ, m, A, $y_1$ have the above significances, and in which y is a whole number from 2 to 20, until the support of formula I in which x=0 and y=20, is obtained, if desired, or with a support of the formula

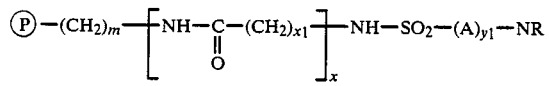 IV wherein P, m, and $x_1$ have the above definitions and x is a whole number from 1 to 20 to obtain an intermediate support of the formula

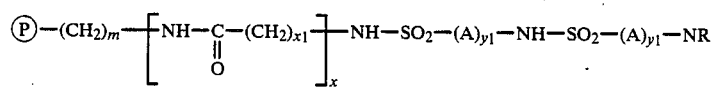

of which the end group —$NH_2$ is liberated to obtain a support of formula I in which Ⓟ, m, $x_1$, a and $y_1$ have the above definitions and x is a whole number from 1 to 20 and y=0, which support in treated again, if necessary, with a product of formula II under the same conditions as previously to obtain an intermediate support of the formula

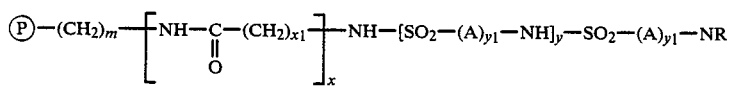

of which the end group $NH_2$ is liberated to obtain a support of formula I in which x is a whole number from 1 to 20 and y is 1, and which process, if necessary, is continued passing through the intermediate supports of the formula (Ⓟ)—$(CH_2)_m$—[NH—C(=O)—$(CH_2)_{x1}$]$_x$—NH—[$SO_2$—$(A)_{y1}$—NH]$_y$—$SO_2$—$(A)_{y1}$—NR in which R, Ⓟ, m, $x_1$, A and $y_1$ have the above definitions and in which x is a whole number from 1 to 20 and y is a whole number from 2 to 20, until a support of formula I in which y=20 is obtained, if desired.

In the compounds of formula II, the protective group of the amine function R is, for example, an acyl radical derived from a carbonic acid such as an ethoxy-carbonyl, benzoyloxy-carbonyl, tertbutyloxycarbonyl (=BOC), p-methoxyloxy-benzyl oxy-carbonyl, or fluorenylmethoxy carbonyl (=FMOC), or a phthalimido, or a radical forming a nitrogen derivative, for example a compound of the formula

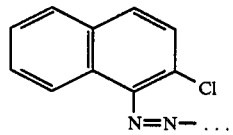

Other radicals can also be used such as substituted or non-substituted aryls or aralkyls for example, benzyl or triphenylmethyl or o-nitro-phenyl sulfenyl.

In a preferred mode of the process, the support of formula III or IV is reacted with a reagent of formula II wherein R is a protective group of FMOC type or a nitrogen group of the formula

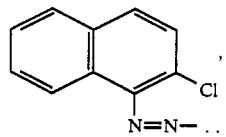

The reaction between the support of formula III or IV and the compound of formula II is carried out in the presence of a chlorinated solvent such as methylene chloride or chloroform and of a tertiary base such as pyridine or triethylamine.

The conditions for deblocking and end amine function of the intermediate supports are variable depending on the protective groups used. Thus, for example: when R is an FMOC group, a strongly basic amine is used such as piperidine but other amines such as pyrrolidine or dialkylamines can also be used. When the phthalamido group is used, it is preferred to use hydrazine hydrate and when a nitrogen group is used such as that mentioned above, it is preferred to use sodium hydrosulfite in the presence of sodium hydroxide. The conditions for deblocking the end amine function in the case of other radicals previously mentioned are known to one skilled in the art.

The compounds of formula II wherein R is an FMOC protective group are prepared by the following reaction diagram; (J.O.C. Vol. 57, 22, 1972):

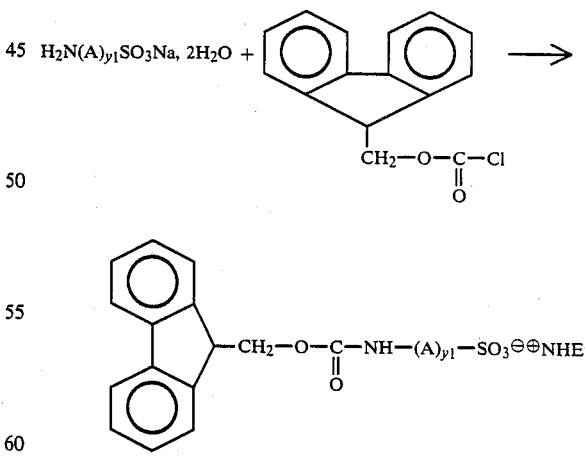

To obtain the compound of formula II, the product thus obtained is reacted with thionyl chloride. When R is phthalimido, the operation is done for example according to the technique described in Synthesis 739, (1976). When R is a nitrogen group such as that previously mentioned, the operation is done for example according to the technique described in Teilheimer Vol. 17, 559, p.

227. In a general way, the protection methods for the amines previously mentioned are well known to an expert.

The supports of formula III used as starting products in the invention process are prepared as indicated in European Pat. No. 0035719. The supports of formula IV used as starting products in the process are prepared according to the process described in Chemistry Letters p. 1597-1600, 1983.

The invention is also concerned with supports of the formula

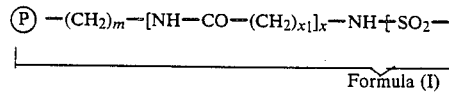
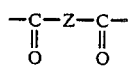

in which $\textcircled{P}$, m, $x_1$, x, $y_1$, y, A and R are defined as above as novel products.

The supports of formula I of the invention enable the synthesis of olignucleotides to be carried out without inconvenience. It is an object of the invention, therefore to use the supports of formula I in the synthesis in solid phase of olignonucleotides by the method with phosphoramidites, with phosphites, with phosphodiesters and with phosphotriesters.

They enable in particular a high standard of first nucleosides and of stable intermediates to be obtained. They can be easily used in the most common methods of synthesis in solid phase of oligonucleotides (method with phosphoramidite, with phosphite, with phosphodiester, with phosphotriester), equally in 3'→5' and in 5'→3' and for all the common purine-type or pyridine-type bases. Furthermore, the final hydrolysis separating the support from the oligonucleotide is easily carried out and at the same time as the deprotection of the phosphate bonds and of the protective groups with purine-type or pyrimidine-type bases.

The invention is concerned quite particularly with the use of supports of formula I in solid synthesis by the method with phosphotriesters and by the method with phosphoramidites and also desoxyribonucleosides and ribonucleosides obtained at the time of synthesis of the oligonucleotides involving the support of formula I The new desoxyribonucleosides and ribonucleosides on supports have the formula

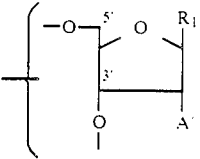
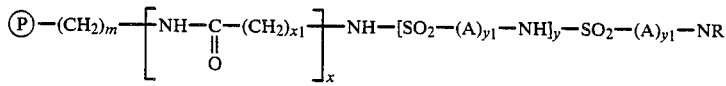

in which the support of formula I is linked to a ribonucleoside or to a desoxyribonucleoside, whether in 3' or in 5', by the intermediary of a $$-\underset{\underset{O}{\|}}{C}-Z-\underset{\underset{O}{\|}}{C}-$$

group, Z being a hydrocarbon of 2 to 20 carbon toms, or phenyl, the hydroxyl function not linked in 3' or 5' to the support possibly being protected and in which A' is either hydrogen if the support of formula I is linked to a desoxyribonucleoside, or $OR_1$ if the support of formula I is linked to a ribonucleoside, $R_1$ being either hydrogen, or a usual protective group of the hydroxyl, $B_1$ is a purine-type or pyrimidine-type base of which the amine function is possibly protected. The subject of the invention is more particularly novel oligodesoxyribonucleosides of the formula

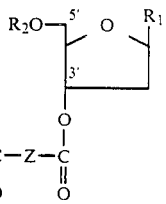
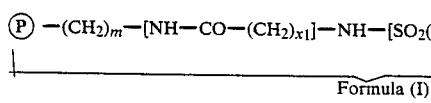
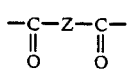

in which the support of formula I is linked to a deoxyribonucleoside in 3' by the intermediary of $$-\underset{\underset{O}{\|}}{C}-Z-\underset{\underset{O}{\|}}{C}-$$

in which Z is a hydrocarbon of 2 to 20 carbon atoms, or phenyl, and the hydroxyl function in 5' is possibly protected by a usual protective group $R_2$, $B_1$ is a purine-type or pyrimidine-type base of which the amine function is possibly protected.

The invention is also concerned with nucleotides obtained by use of supports of formula I for their synthesis.

The subject of the invention is, therefore, new oligodesoxyribonucleotides or oligoribonucleotides on supports wherein the nucleoside is attached either in 3', or in 5', to the support of formula I of the formula

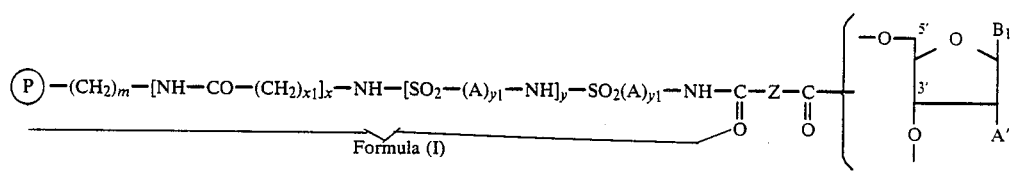

Formula (I)

and is itself linked by phosphodiester or triester bonds of the type

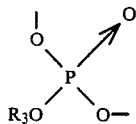

in which $R_3$ is either hydrogen, or a protective group, to other nucleotides carrying $B_1 \ldots B(z-1)$ bases until the last nucleoside with the formula

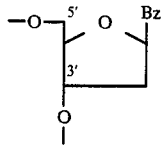

Bz being the last oligodesoxy- or oligoribonucleotide base, the hydroxyl function of the last nucleoside in 5' or in 3' possibly being protected and the different purine-type or pyrimidine-type bases possibly having their amine functions protected.

The preferred oligodesoxyribonucleotides are those on supports of the formula in which the support of formula I is linked in 3' to an oligodesoxyribonucleotide carrying $B_1, B_2 \text{---} B_z$ bases and in which $R_2$ is either hydrogen, or a protective group, $R_3$ is either hydrogen, or a protective group, the purine-type or pyrimidine-type bases having their amine functions possibly protected.

In the desoxyribonucleosides, ribonucleosides, oligodesoxyribonucleotides or oligorbonucleotides on supports previously defined, Z is preferably phenyl or $—(CH_2)_n—$, n being a whole number from 2 to 20. The invention is concerned quite particularly with those for which Z is a $—(CH_2)_2—$ radical. In the ribonucleosides or oligoribonucleotides, defined above, $R_1$ is a usual protective group of the hydroxyl function, such as a pyranyl, silyl or benzyl group.

In the nucleosides or nucleotides previously defined, the $B_1, B_2 \text{---} B_z$ bases represent adenine, guanine (purine-type bases), cytosine, uracil or thymine (pyrimidine-type bases). These bases can also be substituted purine-type or pyrimidine-type bases such as for example 6-methylaminopurine or 6-dimethylaminopurine, 1-methyl guanine, 5-methyl-cytosine, 5-hydroxymethyl cytosine, or dihydrouracil. All the bases called rare or minor that are found in certain nucleic acids can be used.

The protective groups of the nitrogenous functions of these bases are for example benzoyl or isobutyryl groups.

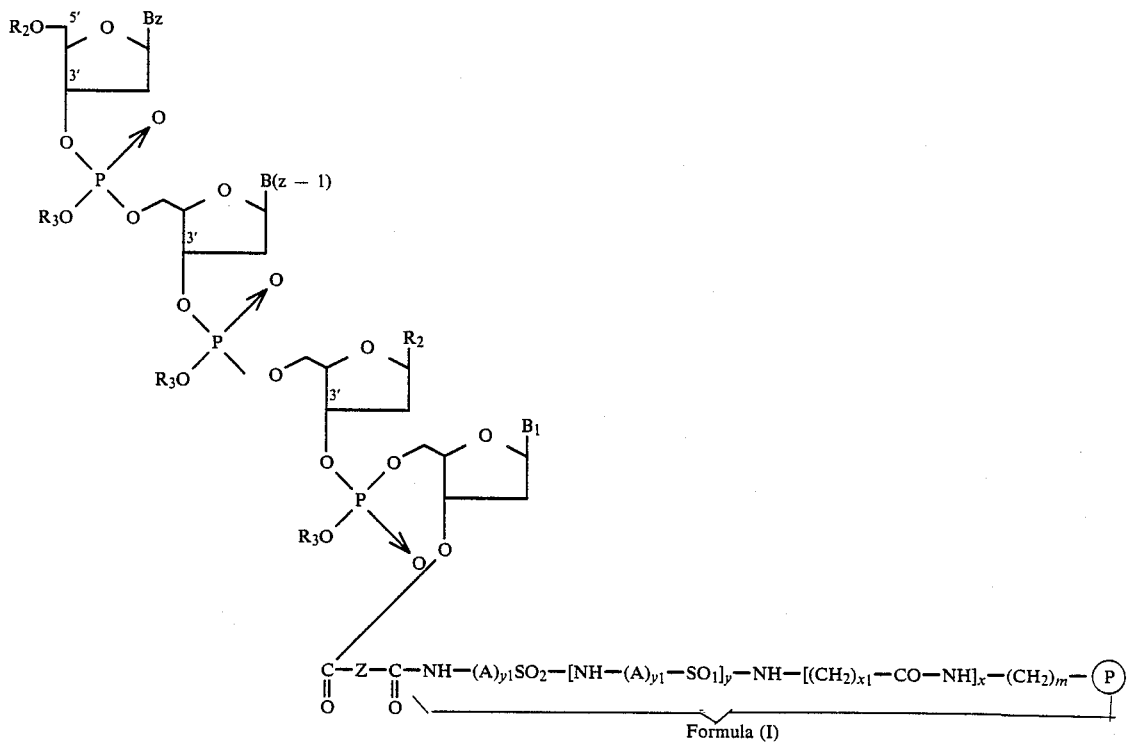

Formula (I)

The protective group $R_2$ of the hydroxyl function in 5' is for example trityl, monomethoxytrityl, dimethoxytrityl or pixyl, The protective group $R_3$ of the hydroxyl functions of phosphate groups is for example methyl, cyanoethyl or an ortho or parachlorophenyl.

In the case of the method with phosphotriesters, $R_3$ is preferred to be an ortho or parachlorophenyl. In the case of the method with phosphoramidites, $R_3$ is preferrably either methyl or cyanoethyl.

The methods of synthesis of polynucleotides previously mentioned are very usual and perfectly known to an expert. A summary of them can be found for example in The Chemical Synthesis of DNA, Aldrichimica Acta, Vol. 16, No. 3, 1983. Hereafter the different stages of the synthesis 3'→5' of oligodesoxyribonucleotides by the method with phosphotriesters and by the method with phosphoramidites are briefly set forth. It goes without saying that the stages are strictly the same for the synthesis of oligodesoxyribonucleotides if the synthesis is done in 5'→3', the protective group of hydroxyl in 3' having to be suitably chosen in this case.

1. Preparation of an activated desoxynucleoside:

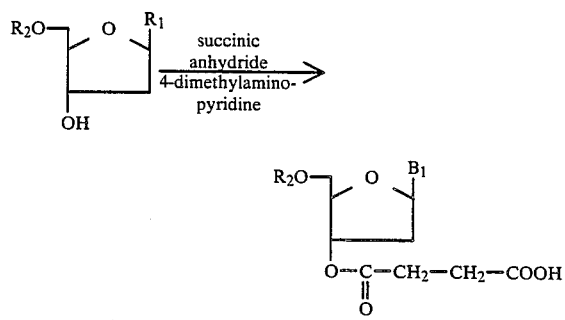

The acid can be used free or activated by a pentachlorophenyl (Itakura et al. Nucl. Ac. Res. 8, 22, 5473, 1980) or p-nitrophenyl (M. H. Caruthers, Chemical and Enzymatic Synthesis of Gene Fragments, H. -Cr. Gassen and A. Lang, Verlag Chemie (1982) p. 71).

2. Condensation of the deoxynucleoside previously prepared on a support of formula I denoted schematically hereafter This condensation is carried out in solution either in dimethylformamide using triethylamine as catalyst for 20 to 24 hours, or in pyridine in the presence of dicyclohexylcarbodiimide for one night to three days or in the presence of dimethylaminopyridine to obtain

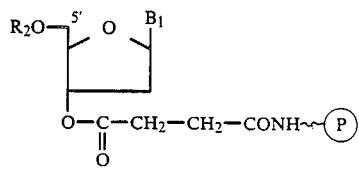

The function 5'OH is deprotected by treatment with a Lewis acid, for example with zinc bromide or with di- or trichloroacetic acid.

3. Extension of the desoxyoligononucleotide chain by the phosphotriester method:

Either monomeric nucleotides or dimeric nucleotides in the form of their triethylammonium salts are used. The dimers are stored in the form of cyanoethyl derivatives and the triethylammonium salt is prepared just before synthesis.

After the protective group of hydroxyl 5' of the first nucleoside fixed on the support has been removed, the dimer prepared at stage 2 in the presence of an activation agent, for example of mesityl sulfonyl 3-nitro 1,2,4-triazole or MSNT or of a mixture of mesityl sulfonyl chloride/N-methyl-imidazole, or a mixture of MSNT/N-methyl-imidazole is condensed in pyridine.

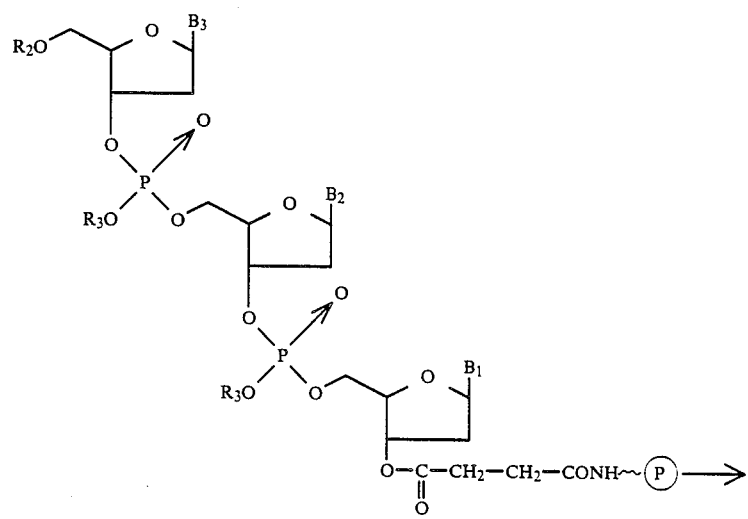

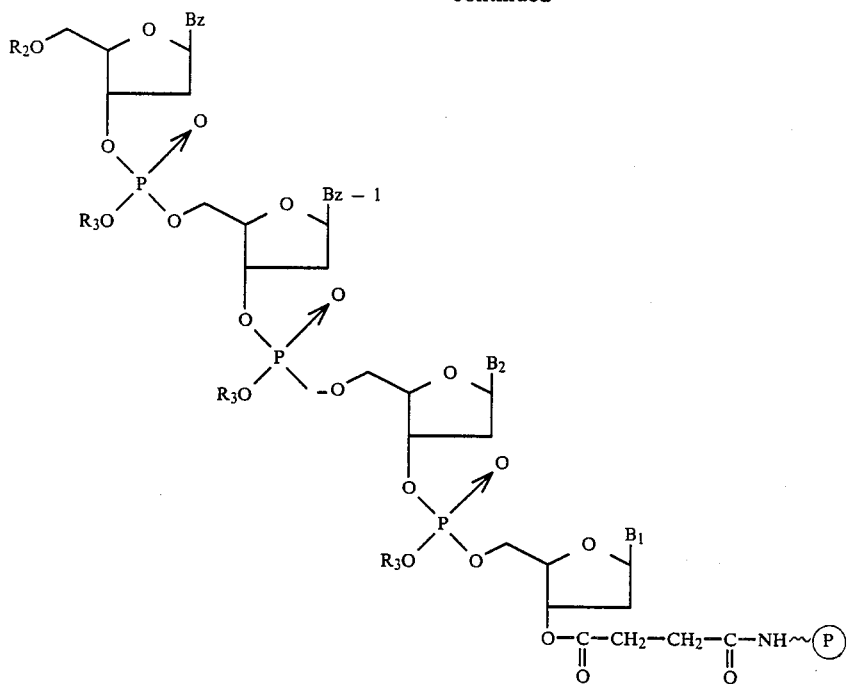
Before each coupling, the protective group in 5' of the last nucleotide attached to the chain is removed.
3'. Extension of the desoxyoligononucleotide chain by the phosphoramidite method
The synthesis diagram is as follows:
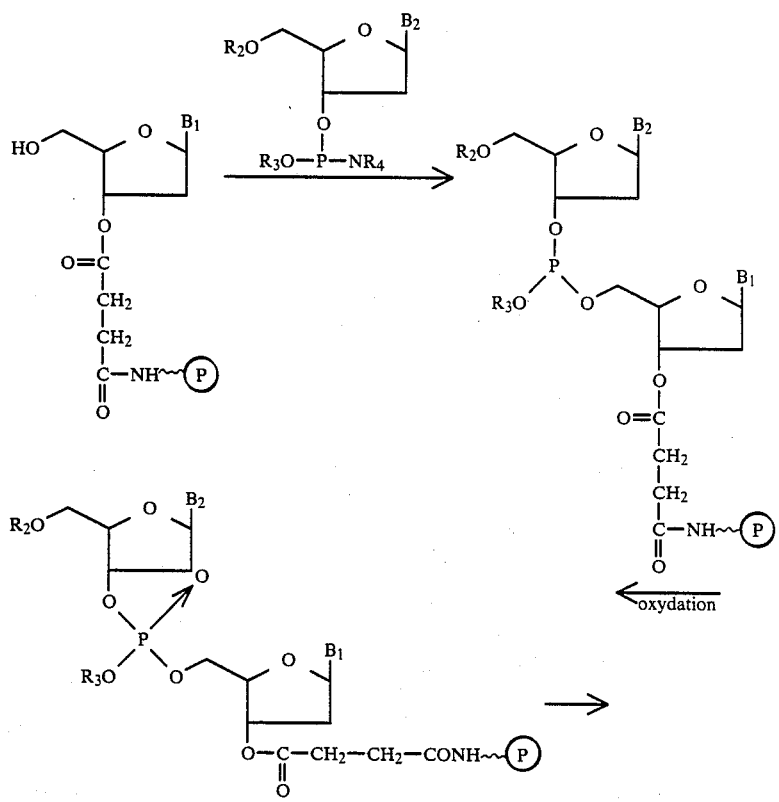

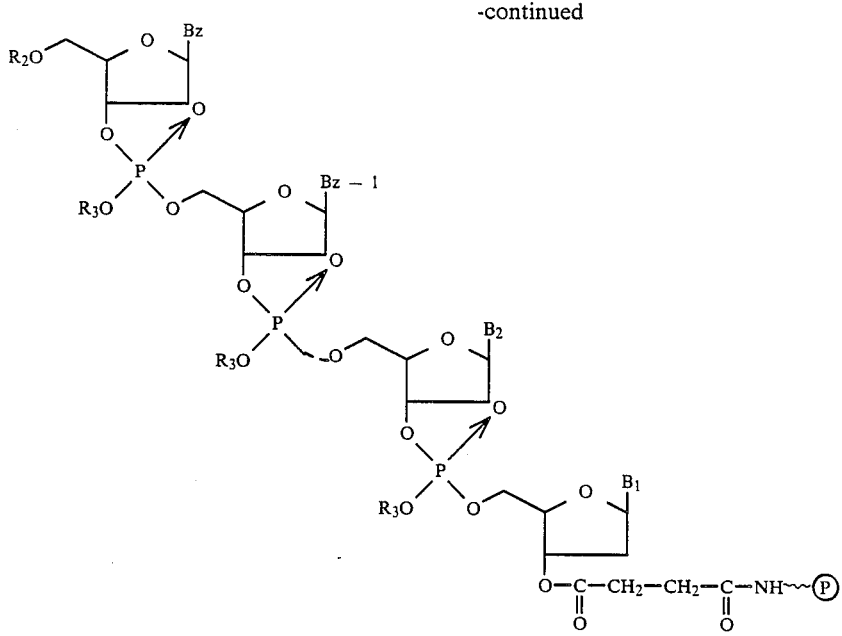

$R_4$ is a divalent group such as morpholino or is two monovalent groups which are alkyl such as isopropyl. The other radicals have the definitions indicated previously. The technique and apparatus marketed as "Applied Biosystems model 381 A" is used.

An acid is reacted on the support of formula I condensed with the first nucleoside carrying the first base $B_1$ necessary for the intended synthesis to free the 5'—OH, then the chosen monomer is fixed in the presence of tetrazole as coupling agent. The immediate oxidation of the intermediate phosphite obtained leads to a phosphate identical to the intermediates of the method with phosphotriesters. The extension of the chain continues with the same strategy for the 2 methods.

4. Deblocking and separation of the support and of the oligonucleotide chain

To obtain the oligonucleotide unprotected, a variable treatment is used adapted to the different protective groups of the functions of the phosphate, amines and hydroxyls at 5'. When the phosphate protective groups is ortho- or parachlorophenyl, a mixture of p-nitrobenzaldoxime and N,N,N',N'-tetramethylguanidine is used, for example, in a mixture of dioxane and water (1-1). This very mild reagent enables the arylic phosphate bonds to be selectively cleaved, relative to the aliphatic phosphates, thus achieving the deblocking of the phosphates without breaking the synthesized chain. After this, concentrated ammonia is reacted for 5 or 6 hours at 60° C. to saponify the amides. In this case, concentrated ammonia can also be used uniquely by heating the reaction medium moderately at 50° C. for 18 to 20 hours. The unique treatment with ammonia can also be used when the phosphate is protected by a cyanoethyl radical.

When the phosphate protective group is methyl, thiophenol is reacted with the nucleotide at ambient temperature and then cleavage of the amides is carried out by concentrated ammonia by heating moderately at 50° C. for 18 to 20 hours as above.

These different treatments enable the oligonucleotide to be obtained unprotected, but equally to be separated from the support. Only the hydroxyl at 5' remains to be deblocked. An acid treatment preferably carried out at the end of the synthesis enables the protective group at 5' to be freed. Acetic acid or di- or tri chloroacetic acid is used. It is necessary to treat the oligonucleotide thus obtained to eliminate all the impurities accumulated during synthesis. Many purification treatments (electrophoresis or chromatography) are then necessary in order to make the desired oligonucleotide. Only by a final stage of sequencing is it possible to know the structure of the oligonucleotide for certain if this should prove necessary.

The supports with the formula I of the invention can also be used for peptide synthesis and this use is therefore also a subject of the invention.

In the following examples there are described several preferred embodiments to illustrate the invention. However, it should be understood that the invention is not intended to be limited to the specific embodiments.

EXAMPLE 1

Preparation of

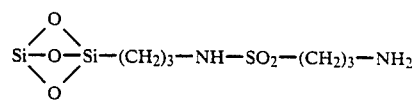

STEP A

Using the procedure of Example 1 of European Pat. No. 0035,719 10 g of silica Vydac A (20μ particle size—300 Å pores) and 11.5 g of 3-aminopropyltriethoxysilane were reacted to obtain a support of the formula

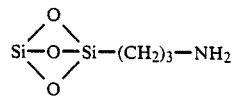

with a $NH_2$ titer of $2 \times 10^{-4}$ eq/g (picric acid method of determination).

STEP B

N,N-diethylethaneamine 3-[-[9H-fluoren-9-yl)-methoxycarbonyl]-amino]-propane-sulfonate Using the procedure of J. Org. Chem., Vol. 57 (1972), No. 22, a mixture of 2.4 g of sodium salt of aminopropanesulfonic acid in its dihydrate form, 19 ml of distilled water and 4.5 g of 9-fluorenylmethyl chloroformate were reacted and the mixture was made alkaline by addition of 2.8 ml of triethylamine. The mixture was stirred for 3 hours and the pH was adjusted to 1 by addition of hydrochloric acid. The mixture was evaporated to dryness under reduced pressure and the residue was extracted with methylene chloride and was vacuum filtered. The solid was washed with methylene chloride and the combined organic phases were evaporated to dryness under reduced pressure to obtain 6.2 g of N,N-diethylethaneamine 3-[-[9H-fluoren-9-yl)-methoxycarbonyl]-amino]-propane-sulfonate.

STEP C 460 mg of N,N-diethylethaneamine 3-[-[(9H-fluoren-9-yl)methoxycarbonyl]-amino]-propane sulfonate were partially dissolved in 5 ml of thionyl chloride and the mixture was stirred for 2 hours and concentrated to dryness under reduced pressure. 1 ml of pyridine, 5 ml of methylene chloride and 500 mg of the support prepared in Step A were added to the residue and the mixture was stirred for 48 hours in darkness at ambient temperature. After filtration, the product was washed successively with dimethylformamide, then with methylene chloride, and dried under reduced pressure to obtain 500 mg of intermediare support titrating $0.28 \times 10^{-4}$ eq/g of $NH_2$ (estimation with picric acid). This was taken up in 2 ml of 20% piperidine in dimethylformamide and the mixture was stirred for 30 minutes and filtered. The product was washed successively with dimethylformamide and with methylene chloride and then dried under reduced pressure to obtain 450 mg of the support titrating $3 \times 10^{-4}$ eq/g of $NH_2$.

EXAMPLE 2

Preparation of the support of the formula

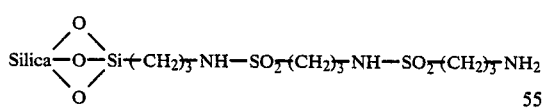

500 mg of N,N-diethylethanamine 3-[-[(9H-fluoren-9-)methoxycarbonyl]-amino]-propane-sulfonate were dissolved in 5 ml of methylene chloride, 2 ml of pyridine and 0.2 ml of thionyl chloride. The solution was stirred for 3 hours, then evaporated to dryness under reduced pressure. The residue was added to 5 ml of methylene chloride, 1 ml pyridine, and 450 mg of the support obtained at Step C of Example 1. The mixture was stirred for 72 hours in darkness at ambient temperature and was filtered. The product was washed with 100% ethanol then with methylene chloride and dried under reduced pressure to obtain 440 mg of intermediate support titrating $3 \times 10^{-5}$ eq/g in $NH_2$. The product was taken up in 2 ml of 20% piperidine in dimethylformamide and the mixture was stirred for 30 minutes and was filtered. The product was washed successively with dimethylformamide, then with methylene chloride and dried under reduced pressure to obtain 380 mg of the above support having a titre of $NH_2$ of $2.8 \times 10^{-4}$ equivalent/gram.

EXAMPLE 3

Preparation of the support of the formula

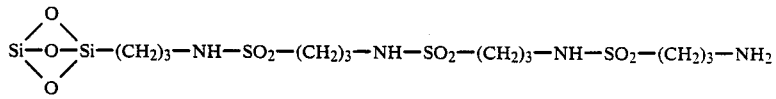

Using the procedure of Example 1, 500 mg of N,N-diethylethanamine 3-[-[(9H-fluoren-9-yl)-methoxycarbonyl]-amino]-propane-sulfonate and 200 mg of the support of Example 2 were reacted to obtain 200 mg of intermediate support having a titre of $NH_2$ of $0.3 \times 10^{-4}$ eq/g, and then, 190 mg of the expected support were obtained having a titre of $NH_2$ of $2.3 \times 10^{-4}$ eq/g.

EXAMPLE 4

Preparation of the support of the formula $$Si{-}O{-}Si{-}(CH_2)_3{-}NH{-}\underset{O}{\overset{\parallel}{C}}{-}(CH_2)_{10}{-}NH{-}SO_2{-}(CH_2)_3{-}NH_2$$

The starting support was a support with the formula $$Si{-}O{-}Si{-}(CH_2)_3{-}NH{-}\underset{O}{\overset{\parallel}{C}}{-}(CH_2)_{10}{-}NH_2$$

titrating $3 \times 10^{-4}$ equivalent/gram in $NH_2$ prepared by the process described in Chemistry Letters, p. 1597-1600, 1983, starting with the support:

$$Silica{-}O{-}Si{-}(CH_2)_3{-}NH_2$$

prepared in Step A of Example 1. 200 mg of the starting support were mixed with 5 ml of chloroform, 1 ml of acetonitrile and 300 mg of phthalimido-ethane sulfochloride and 0.28 ml of triethylamine were then added dropwise with stirring. The mixture was refluxed 2 hours and then stirred over night at ambient temperature. The mixture was filtered and the product was washed with chloroform and dried under reduced pressure. If a test with Ninhydrin was positive, the silica was put back into reaction in the preceding conditions until the test was negative. The silica was taken up in 5 ml of methanol, 1 ml of 100% hydrazine hydrate and 0.15 ml of water with stirring and the mixture was refluxed for 2 hours and filtered. The product was washed with a mixture of methylene chloride and methanol (1-1), and dried under reduced pressure to obtain 185 mg of the above support titrating $3 \times 10^{-4}$ equivalent/gram in $NH_2$.

Preparation of phthalimido ethane sulfochloride

Using the process of Synthesis 739 (1976), 2.9 g of the potassium salt of phthalimido ethane sulfonic acid, 10 ml of phosphorus oxychloride and 2 g of phosphorus pentachloride were reacted to obtain 1.9 g of phthalimido ethane sulfochloride melting at 162° C.

EXAMPLE 5

Preparation of the support of the formula

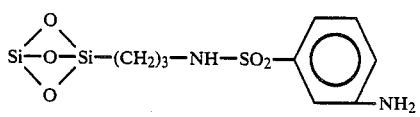

Step A

Disodium salt of 3-[(2-hydroxy-1-naphthalenyl)azo]-benzene sulfonic acid 3.46 g of metasulfanilic acid were mixed in 25 ml of 2N hydrochloric acid cooled to 0°/+2° C., and over 90 minutes, 1.65 g of sodium nitrite in solution in 8 ml of water was added dropwise. After stirring for 15 minutes, the mixture was poured into a solution prepared at ambient temperature of 3.17 g of β-naphthol, 22 ml of N sodium hydroxide and 1.7 g of sodium carbonate. After stirring for 15 minutes, the precipitate was separated, washed with iced water and dried under reduced pressure at 80° C. to obtain 6.7 g of disodium salt of 3-[(2-hydroxy-1-naphthalenyl)-azo]-benzene sulfonic acid.

STEP B

3-[(2-chloro-1-naphthalenyl)azo]-benzene sulfonic acid chloride 5.7 g of the acid of Step A, 25 ml of phosphorus oxychloride and 3.2 g of phosphorus pentachloride were mixed together and the phosphorus oxychloride was eliminated by distilling under reduced pressure. The residue was taken up in 50 ml of methylene chloride and after filtering and concentrating to dryness under pressure, the residue was crystallized from acetone. After drying at 50° C. under reduced pressure, 3.25 g of 3-[(2-chloro-1-napthalenyl)azo]-benzene sulfonic acid chloride were obtained.

| IR Spectrum: | |
| --- | --- |
| Aromatic | $1618 \text{ cm}^{-1}$ |
| conjugated system | $1582 \text{ cm}^{-1} - 1503 \text{ cm}^{-1}$ |
| $SO_2$ | $1330 \text{ cm}^{-1} - 1180 \text{ cm}^{-1} - 1170 \text{ cm}^{-1}$ |

STEP C

Preparation of the support of the formula

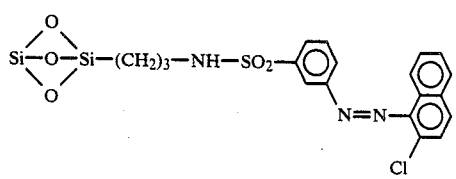

A mixture of 300 mg of the support prepared in Step A of Example 1, 500 mg of 3-[(2-chloro-1-naphthalenyl)azo]-benzene sulfonic acid chloride, 3 ml of methylene chloride, 0.6 ml of acetonitrile and 0.3 ml of triethylamine was stirred for 24 hours and then was filtered. The product was washed successively with methylene chloride, then with methanol, and dried under reduced pressure at ambient temperature to obtain 250 mg of intermediate support having a titre in $NH_2$ of $5 \times 10^{-6}$ eq/g.

STEP D

Preparation of the support of the formula

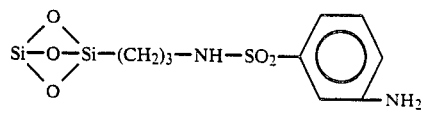

A mixture of 200 mg of the support of Step C in 5 ml of 0.1N sodium hydroxide was heated to 50° C. and 1 g of sodium hydrosulfite was added. The mixture was held at 120° C. for 30 minutes, then was cooled and the support obtained was separated, washed successively with water, with methanol and then with methylene chloride. After drying under reduced pressure at ambient temperature, 81 mg of the above support having a titre in $NH_2$ of $7.2 \times 10^{-5}$ equivalent/gram were obtained.

EXAMPLE 6

Preparation of the support of the formula

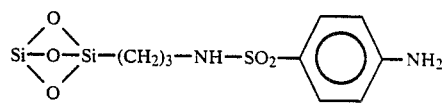

STEP A

Disodium salt of 4-[(2-hydroxy-1-naphthalenyl)azo]-benzenesulfonic acid

Using the procedure of Step A of Example 5, 3.46 g of sulfanilic acid in 50 ml of N hydrochloric acid were reacted to obtain 7.15 g of disodium salt of 4-[(2-hydroxy-1-naphthalenyl)azo]-benzenesulfonic acid which was used as is for the following step.

STEP B

4-[(2-chloro-1-naphthalenyl)-azo]-benzene sulfonic acid chloride

Using the procedure of Step B of Example 5, 7.15 g of the product of Step A, 32 ml of phosphorus oxychloride and 8 g of phosphorus pentachloride were reacted to obtain 4.25 g of 4-[(2-chloro-1-naphthalenyl)-azo]-benzene sulfonic acid chloride.

IR Spectrum:

| | |
|---|---|
| aromatics | 1585 cm$^{-1}$ |
| conjugated system | 1804 cm$^{-1}$ |
| SO$_2$ | 1381 cm$^{-1}$ — 1181 cm$^{-1}$ |

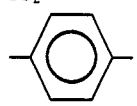

STEP A

Preparation of the support of the formula

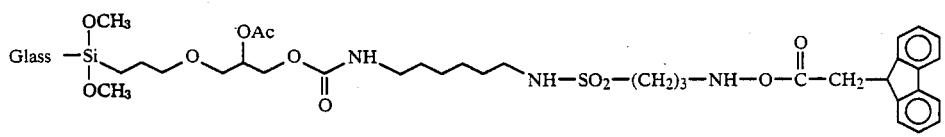

A mixture of 1 g of 9-fluorenylmethyl carbamate of 3-aminopropyl sulfonic acid chloride obtained in Step B of Example 1, 4 ml of acetonitrile, 200 mg of C.P.G. glass with long alkylamine chain and 2 ml of triethylamine was stirred for 12 hours and after filtration, the product was washed successively with acetonitrile, water, methanol and finally with methylene chloride, followed by drying under reduced pressure at ambient temperature to obtain 190 mg of crude product. The residue was taken up in 10 ml of pyridine with 1 ml of phenyl isocyanate. The mixture was filtered and the product was washed, first with a mixture of methylene chloride and methanol (1-1), then with methylene chloride alone, and finally dried under reduced pressure at ambient temperature to obtain 180 mg of the above product.

STEP B

Preparation of the support

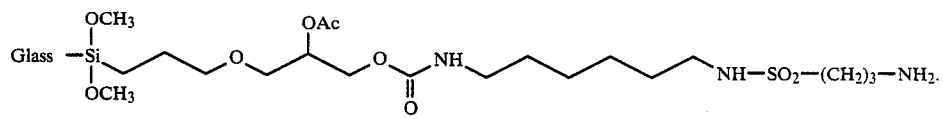

The 180 mg of the product of Step A were triturated 3 times with 1 ml of a dimethylformamide-piperidine mixture (9-1). After separating, washing with methanol, then with methylene chloride, and drying under reduced pressure at ambient temperature, 170 mg of the above support having a titre in NH$_2$ of $1.8 \times 10^{-5}$ equivalent/gram were obtained.

Synthesis of oligonucleotides by the phosphotriester method

The support of formula I was arranged in a minicolumn between two filters of polyfluoroethylene which were kept in a fixed position by two hollow pistons. The assembly was closed at the top by a screw stopper provided with a septum through which the coupling mixture was introduced with a syringe. The apparatus used was similar to that described in "Chemical and Enzymatic Synthesis of Gene Fragments", H-Cr. Gassen, A. Lang, Verlag Chemie 82, p. 14. All the repetitive operations of washing and introduction of reagents were automated and the number of nucleotides to be introduced for the totality of the synthesis would be programmed. The introduction of the nucleotide was the only mammal operation to be carried out with the syringe. The amount of support of formula I was placed in

STEP C

Preparation of the support of the formula

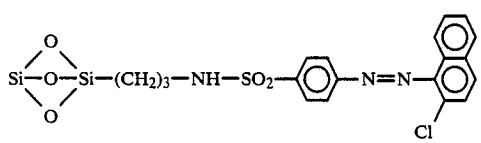

Using the procedure of Step C of Example 5, 400 mg of the support of Step A of Example 1 and 734 mg of 4-[(2-chloro-1-naphthalenyl)-azo]-benzene sulfonic acid chloride were reacted to obtain 390 mg of intermediate support having a titre in NH$_2$ of $5 \times 10^{-6}$ equivalent/gram and $6 \times 10^{-6}$ equivalent/gram.

STEP D

Preparation of the support of the formula

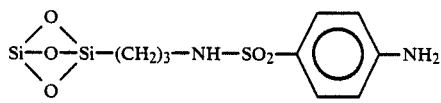

200 mg of the support of Step C were heated to 50° C. in 10 ml of 0.1N sodium hydroxide and 1 g of sodium hydrosulfite was added. The mixture was stirred at 50° C. for 20 minutes, then the support obtained was separated, washed successively with water, with methanol and with methylene chloride, then dried under reduced pressure at ambient temperature to obtain 160 mg of the above support having a titre in NH$_2$ of $8 \times 10^{-5}$ mole/g.

EXAMPLE 7

Preparation of the support of the formula

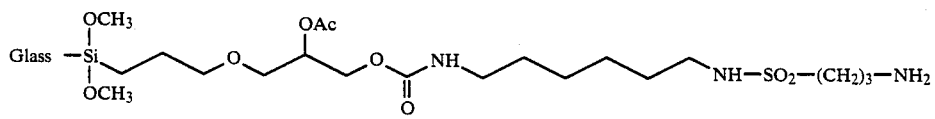

the reactor condensed with the first nucleoside carrying the first base $B_1$ necessary for the intended synthesis (25 to 150 mg). The desired parameters were programmed suitably, particularly the number of nucleotides to be attached successively, then the following automatic cycle was begun:

STAGE 1

| Solvent | how introduced | Time |
| --- | --- | --- |
| Pyridine | Continuous flow: 1 cm³/min. | 5 min. |
| Phenyl isocyanate at 10% in pyridine | Programmed fractions | 10 min. |
| Pyridine | Continuous flow: 1 cm³/min. | 5 min. |
| Methylene chloride | Continuous flow: 2 cm³/min. | 3 min, |
| Dichloro acetic acid 10% in methylene chloride | Continuous flow: about 2 cm³/min | 4.5 min. |
| DMF | Continuous flow: 1 cm³ | 5 min. |
| Pyridine | Continuous flow: 1 cm³/min. | 5 min. |
| Coupling | By syringe | 15 min. to 1 hr. |

STAGE 2

As many cycles identical to the first were carried out as was necessary to obtain the nucleotide desired. The solvents utilized in this synthesis cycle must be very pure and anhydrous. The UV estimation of the quantity of tritylium ions carried out after detritylation enabled the yield of each coupling to be determined.

The coupling mixture was prepared just before use and comprised 10 equivalents of the triethylammonium salts of the monomeric or dimeric nucleotide (relative to the amount of the first nucleoside present on the solid support). 30 equivalents of mesityl sulfonyl 3-nitro 1,2,4-triazole or MSNT in anhydrous pyridine (0.3 ml for about 50 mg of dimer). This mixture was transferred in a syringe under an anhydrous argon atmosphere and was added in three lots at regular intervals.

To obtain the oligonucleotide totally deprotected, it was then necessary to carry out a certain number of treatments which are well known and are described, for example, in "Chemical and Enzymatic Synthesis of Gene Fragments", H-Cr. Gassen and A. Lang, Verlag Chemie 82, pages 2 to 42.

The following are the treatments:

(1) Cleave the nucleotide from its solid support and deprotect the phosphates

A treatment is carried out with a 0.3M solution of 1,1,3,3-tetramethyl guanidinium o-nitrobenzaldoximate in a dioxane-water mixture (1-1) as taught in Nucleic Acids Research, Vol. 9 No. 18, 1981, p. 4611. This very mild reagent thus enabled the aryl phosphate bonds to be cleaved selectively relative to the aliphatic phosphates, thus achieving the deblocking of the phosphates without breaking the synthesized chain.

(2) Deblocking the amine functions of the nitrogen bases

A treatment was carried out with saturated (37%) $NH_4OH$ solution and all the amines of the nitrogen bases were thus liberated. Treatment 1 could also be omitted and the treatment with $NH_4OH$ prolonged which caused the same reactions.

(3) Deblocking the function at 5' of the last nucleotide

A treatment is carried out with a $CH_3COOH$-water mixture (4-1). After concentrating to dryness under reduced pressure, the residue was taken up in water and the solution was extracted with ether to eliminate all the reagents and the cleavage products. The oligonucleotide with y links obtained contained numerous impurities (nucleotides with y-2, y-4, —links, and various degradation products). Obtaining the product sought required many successive stages of purification by -chromatography on gels, —HPLC-electrophoresis and sequencing. This latter process gives the sequence of the monomeric nucleotides unambiguously and in order and these processes are quite conventional.

EXAMPLE 8

Oligo-desoxyribonucleotides synthesized with the support of Example 1

(1)

Preparation of 5'-dimethoxytrityl-2'-deoxythymidine-3'-p-nitrophenyl succinate.

The method used is as described by Caruthers, "Chemical and Enzymatic Synthesis of Gene Fragments" and Gassen et al Verlag Chemie (1982), p. 71. 1.557 g of 5'dimethoxytrityl-2'-deoxythymidine-3'-succinic acid, 10 ml of anhydrous dioxane, 0.5 ml of anhydrous pyridine, 369 mg of p-nitrophenol, and 585 mg of dicyclohexyl carbodiimide in solution in 2.5 ml of anhydrous dioxane were reacted to obtain 1.150 g of 5'-dimethoxytrityl-2'-deoxythymidine-3'p-nitrophenyl succinate.

(2)

Condensation between the support of Example 1 and the activated thymidine succinate.

At ambient temperature and in darkness, 70 mg of the support of Example 1 titrating $2 \times 10^{-4}$ eq/g in $NH_2$, 100 mg of the activated thymidine succinate prepared above, i.e., about 11 equivalents, 150 mg of dicyclohexylcarbodiimide in 2.5 ml of pyridine were reacted and after filtering and washing with methylene chloride and drying under reduced pressure, 60 mg of the expected condensed support having a titre in dimethoxytrityl of $2 \times 10^{-5}$ eq/g. were obtained.

(3) Starting with the support of Example 1, condensed with thymidine succinate, and by utilizing three dimers, there was obtained the oligo-desoxyribonucleotide: b 5'-d (TTA AA CT). The coupling agent utilized was MSNT.

EXAMPLE 9

Oligo-desoxyribonucleotides synthesized with the support of Example 2

(1)

Condensation between the support of Example 2 and 5'-dimethoxytrityl-2'-deoxythymidine-3'-succinic acid.

At ambient temperature and in darkness, 170 mg of the support of Example 2, 300 mg of 5'-dimethoxytrityl-2'-deoxythymidine-3'-succinic acid and 415 mg of dicyclohexylcarbodiimide in 3 ml of pyridine were stirred together for 72 hours. After separating, washing successively with pyridine, a mixture of methylene chloride and methanol, then with methylene chloride and drying under reduced pressure, 140 mg of the condensed support having a titre of dimethoxytrityl of $3.8 \times 10^{-5}$ eq/g were obtained.

(2)

Starting from the condensed support prepared above, by using two dimers in the presence of -MSNT, the oligodesoxyribonucleotide 5'-d (TTA AA) was obtained. A second trial was carried out in the presence of mesitylene sulfonyl chloride/N-methyl-imidazole mixture using 3 dimers and the polydesoxyribonucleotide 5'-d (TTA AA CT) was obtained.

EXAMPLE 10

Oligodesoxyribonucleotides synthesized with the support of Example 3

(1)

Condensation between the support of Example 3 and 5'-dimethoxytrityl-2'-desoxythymidine-3'-succinic acid At ambient temperature and in darkness, 174 mg of the support of Example 3, 260 mg of 5'-dimethoxytrityl-2'-desoxythymidine-3'-succinic acid and 200 mg of dicyclohexylcarbodiimide in 3 ml of pyridine were stirred for 72 hours and after separating, washing successively with pyridine, with a mixture of methylene chloride and methanol, then with methylene chloride and drying under reduced pressure, 160 mg of the condensed support having a titre of dimethoxytrityl of 3 $10^{-5}$ eq/g were obtained.

(2)

Starting with the condensed support prepared above and 2 dimers in the presence of MSNT, the oligodesoxyribonucleotide 5'-d (TTA AA) was obtained. A second trial was carried out in the presence of a mesitylene sulfonyl chloride/N-methyl-imidazole mixture and the oligodesoxyribonucleotide 5'-d (TTA AA CT) were obtained.

EXAMPLE 11

Oligodesoxyribonucleotides synthesized with the support of Example 4

(1)

Condensation between the support of Example 4 and 5'-dimethoxytrityl-2'-deoxyguanosine-3'-succinic acid was effected by the process of stages 1) of Examples 9 and 10, and the expected condensed support having a titre of dimethoxytrityl of $1.1 \times 10^{-4}$ eq/g was obtained.

(2)

Starting with the condensed support prepared above and a monomer and a dimer, the oligodesoxyribonucleotide 5'-d (G-ACT) was obtained. The coupling agent was a mesitylene sulfonyl choride / N-methylimidazole mixture.

EXAMPLE 12

Oligodesoxyribonucleotides synthesized with the support of Example 5

(1)

Condensation between the support of Example 5 and activated thymidine succinate was effected by the process of stage 2 of Example 8, using 5'-dimethoxytrityl-2'-deoxythymidine-3'-paranitrophenyl succinate prepared in step 1 of Example 8 and the support of Example 5. The desired condensed support having a titre of dimethoxytrityl of $2.8 \times 10^{-5}$ eq/g was obtained.

(2)

Starting with the above condensed support and 4 dimers, oligodesoxyribonucleotide 5'-d (CATT-TACTT) was prepared. The coupling agent used was a MSNT/N-methyl-imidazole mixture.

EXAMPLE 13

Oligodesoxyribonucleotides synthesized with the support of Example 6.

(1)

Condensation between the support of Example 6 and activated thymidine succinate was effected by the process of stage 2 of Example 8 using 5'-dimethoxytrityl-2'-deoxythymidine-3'-paranitrophenyl succinate prepared in stage 1 of Example 8 and the support of Example 6. The desired condensed support having a titre of dimethoxytrityl of $7 \times 10^{-5}$ eq/g was obtained.

(2)

By using the above condensed support and 3 dimers in the presence of a MSNT/N-methyl-imidazole mixture, the oligodesoxyribonucleotide 5'-d (CATTTAT) was obtained. A second trial was carried out and the oligodesoxyribonucleotide 5'-d (TCTTCT) was obtained.

EXAMPLE 14

Oligodesoxyribonucleotides synthesized by using the support of Example 7

(1)

5'-dimethoxytrityl-2'-N-benzoyldesoxycytidine-3'-paranitrophenyl succinate.

The method used was Caruthers, "Chemical and Enzymatic Synthesis of Gene Fragments", Gassen et al, Verlag Chemie (1982). 71, 4.16 g of 5'-dimethoxytrityl-2'-deoxy-N-benzoylcytidine-3'-succinic acid, 25 ml of anhydrous dioxane, 0.8 ml of pyridine, 1.16 g of p-nitrophenol, and 1.83 g of dicyclohexylcarbodiimide in 8.33 ml of pyridine were reacted to obtain 3.6 g of oligodesoxyribonucleotides synthesized by using the support of Example 7.

(2)

Condensation between the support of Example 7 and the above activated cytidine succinate.

Using the procedure of stage 2 of Example 8, the above activated cytidine succinate and the support of Example 7 were reacted to obtain the desired condensed support having a titre of dimethoxytrityl of $1.5 \times 10^{-5}$ eq/g.

(3)

Starting with the above condensed support and 3 dimers and a MSNT/N-methyl-imidazole mixture as coupling agent, the oligodesoxyribonucleotide 5'-d (CATTAC) was obtained. A second trial with 2 dimers enabled the oligodesoxyribonucloeotide 5'-d (TTAAC) to be obtained.

EXAMPLE 15

Oligodesoxyribonucleotides synthesized by using the support of Example 1 by the method with phosphoramidite (1)

Condensation between the support of Example 1 and activated cytidine succinate.

Using the procedure of stage 2 of Example 8, the support of Example 1 and activated cytidine succinate of Example 14 were reacted to obtain the desired condensed support having a titre of dimethoxytrityl of $1.8 \times 10^{-5}$ eq/g.

(2)

The operation was done according to the technique indicated above with the "Applied Biosystems" apparatus, using the condensed support of stage 1 above and 11 monomers and by choosing a methyl radical as protective group of the hydroxyl function of the phosphate group to obtain the oligodesoxyribonucleotide 5'-d (GTACTCAGATAC). A second trial carried out under the same conditions but using cyanoethyl as protective group of the hydroxyl function of the phosphate group using 5 monomers and the oligodesoxyribonucleotide 5'-d (GACTTC) was obtained.

Various modifications of the products and processes of the invention may be made without departing from the spirit or scope thereof and it should be understood that the invention is intended to be limited only as defined in the appended claims.

What we claim is:

1. A support of the formula

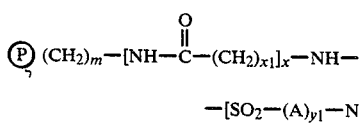

$$-[SO_2-(A)_{y1}-NH]_y-SO_2-(A)_{y1}-NH_2 \qquad I$$

wherein Ⓟ is a material selected from the group consisting of functionalized glass micropellets, silica functionalized by aminoalkyl trialkoxysilane capable of producing for

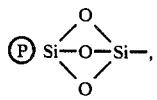

Kieselguhr, polytetrafluoroethylene, cellulose and metallic oxides, m is an integer from 1 to 20. A is selected from the group consisting of alkyl of 1 to 20 carbon atoms, saturated cycloalkyl of 3 to 12 carbon atoms, phenyl and 5 to 6 member heterocycles, x and y are an integer from 0 to 20, $x_1$ is an integer from 1 to 20 and $y_1$ is an integer from 0 to 10.

2. A support of claim 1 selected from the group consisting of

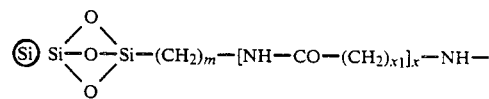

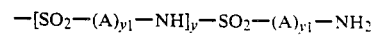

and

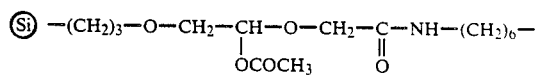

$$-[NH-CO-(CH_2)_{x1}]_x-NH-[SO_2-(A)_{y1}-NH]_y-$$

$$-SO_2-(A)_{y1}-NH_2$$

wherein m, x, x, $y_1$, y and A are defined as in claim 1.

3. A support of claim 1 wherein Ⓟ is a support having a homogeneous particle size.

4. A support of claim 1 wherein m is a whole number from 1 to 10.

5. A support of claim 1 wherein $x_1$ is a whole number from 1 to 10 and x is a whole number from 0 to 10.

6. A support of claim 1 wherein A is —CH_2— or phenyl.

7. A support of claim 1 wherein $y_1$ is a whole number from 0 to 5 and y is a whole number from 0 to 10.

8. A support of claim 1 wherein Ⓟ is

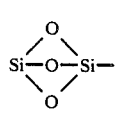

and m is 3.

9. A support of claim 1 selected from the group consisting of

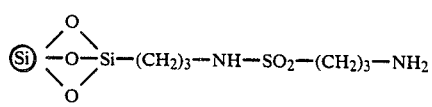

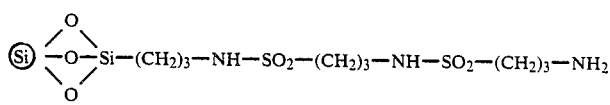

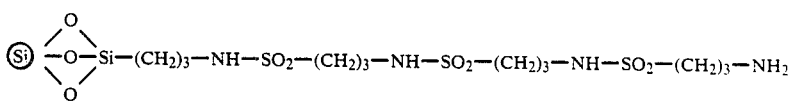

-continued

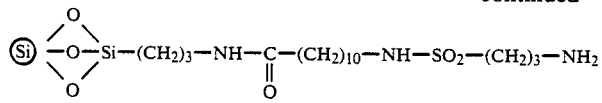

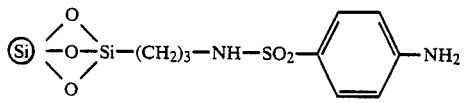

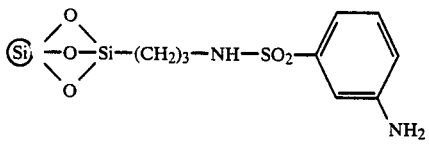

Si being VYDAC A silica and a support of the formula

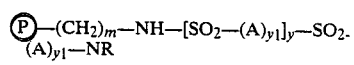

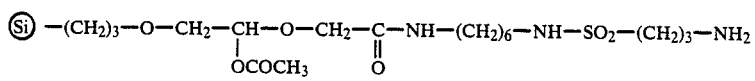

10. A process for the preparation of a support of claim 1 comprising reacting a compound of the formula RN—(A)$_{y1}$—SO$_2$Cl      II wherein R is a monovalent or divalent protective group of the amine function, A and y$_1$ having the above definition in the presence of a tertiary amino base with either a support of the formula

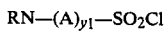      III wherein ⓟ and m have the above definition to obtain an intermediate support of the formula

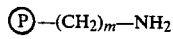

of which the end —NH$_2$ group is liberated to obtain thus a support of formula I in which ⓟ, m, A, y$_1$ have the previous significances, and in which x=0 and y=0, which support, if necessary, is reacted again with a product of formula II under the same conditions as before to obtain an intermediate support of the formula

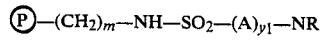

which the end group —NH$_2$ is liberated again to obtain a support of formula I in which x=0 and y=1, which process, if necessary, is continued successively, passing through the intermediate supports with the formula

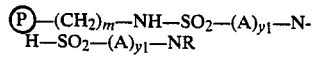

in which R, ⓟ, m, A, y$_1$ have the above significances, and in which y is a whole number from 2 to 20, until the support of formula I in which x=0 and y=20, is obtained, if desired, or with a support of the formula

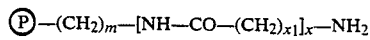      IV wherein p, m, and x$_1$ have the above definitions and x is a whole number from 1 to 20 to obtain an intermediate support of the formula

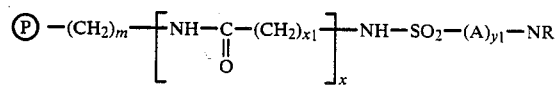

of which the end group —NH$_2$ is liberated to obtain a support of formula I in which ⓟ, m, x$_1$, a and y$_1$ have the above definitions and x is a whole number from 1 to 20 and y=0, which support is treated again, if necessary, with a product of formula I under the same conditions as previously to obtain an intermediate support of the formula

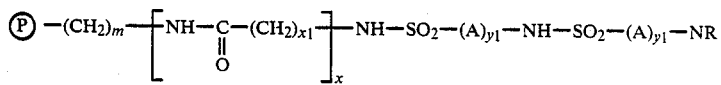

of which the end group NH$_2$ is liberated to obtain a support of formula I in which x is a whole number from 1 to 20 and y is 1, and which process, if necessary, is continued passing through the intermediate supports of the formula

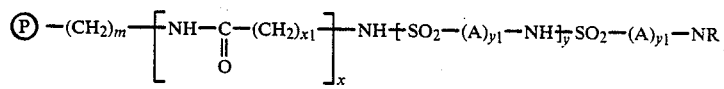

in which R, ⓟ, m, x$_1$, A and y$_1$ have the above definitions and in which x is a whole number from 1 to 20 and y is a whole number from 2 to 20, until a support of formula I in which y=20 is obtained, if desired.
11. An intermediate support of the formula
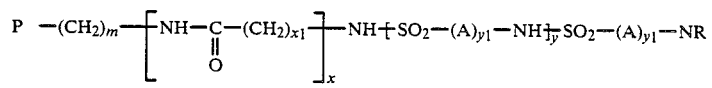
wherein $P$, $m$, $x_1$, $x$, $y_1$ $y$, $A$ and $R$ are defined as in claim 1.
* * * * *